United States Patent [19]
von Daehne et al.

[11] 3,951,957
[45] Apr. 20, 1976

[54] CHLOROMETHYL ESTER OF PENICILLINS

[75] Inventors: Welf von Daehne, Rungsted Kyst; Erling Knud Frederiksen, Holte; Wagn Ole Godtfredsen, Varlose; Schneur Rachlin, Horsholm, all of Denmark

[73] Assignee: Lovens Kemiske Fabrik Produktionsaktieselskab, Ballerup, Denmark

[22] Filed: June 18, 1974

[21] Appl. No.: 480,559

Related U.S. Application Data

[62] Division of Ser. No. 121,547, March 5, 1971, Pat. No. 3,850,908.

[30] Foreign Application Priority Data

Mar. 12, 1970 United Kingdom............... 11995/70
Aug. 26, 1970 United Kingdom............... 41667/70

[52] U.S. Cl.............................. 260/239.1; 424/271
[51] Int. Cl.[2]...................................... C07D 499/44
[58] Field of Search................................ 260/239.1

[56] References Cited
UNITED STATES PATENTS 3,850,908   11/1974   von Daehne et al............. 260/239.1

*Primary Examiner*—Nicholas S. Rizzo
*Attorney, Agent, or Firm*—Dennis P. Clarke

[57] ABSTRACT

New penicillin esters and their salts together with methods for, and intermediates in the preparation thereof, the esters having the formula:

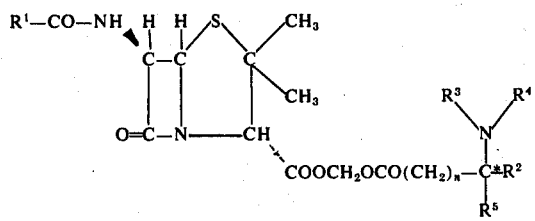

in which formula the asterisk indicates the possibility of an asymmetric carbon atom, $n$ indicates an integer from 0 to 5, $R^1$ represents a group, which together with —CO— forms the side chain of any of the known semisynthetic, biosynthetic, and natural penicillins; $R^2$ has any of the following meanings: hydrogen, an aliphatic, an aromatic, a heterocyclic group, and an aromatically substituted aliphatic group; each of $R^3$, $R^4$, and $R^5$ represents hydrogen, or a lower aliphatic group with the provision that $R^2$ and $R^5$ together with the carbon atom between them can form a 5-, 6-, or 7-membered carbocyclic ring, and either $R^3$ and $R^4$, or $R^4$ and $R^5$ together with the nitrogen atom can form a ring system.

1 Claim, No Drawings

CHLOROMETHYL ESTER OF PENICILLINS

This is a division of application Ser. No. 121,547, filed Mar. 5, 1971, now U.S. Pat. No. 3,850,908.

This invention relates to a new series of penicillin esters of the general formula

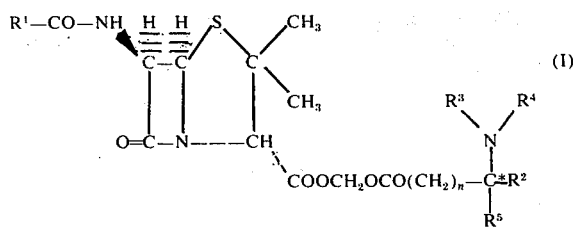

in which formula the asterisk indicates the possibility of an asymmetric carbon atom, $n$ indicates an integer from 0 to 5, $R^1$ represents radicals known from semi-synthetic, biosynthetic, and natural penicillins; $R^2$ represents hydrogen, an aliphatic, an aromatic, or a heterocyclic radical, or an aromatically substituted aliphatic radical; $R^3$, $R^4$, and $R^5$ represent hydrogen, or a lower aliphatic radical, or $R^2$ and $R^5$ together with the carbon atom between them can form a 5-, 6-, or 7-membered carbocyclic ring, and either $R^3$ and $R^4$, or $R^4$ and $R^5$ together with the nitrogen atom can form a ring system; to salts thereof and to methods for the preparation of the esters and salts.

As illustrative examples of the meanings of the substituents can be mentioned that $R^1$ in particular can be a substituted or unsubstituted benzyl radical, a phenoxymethyl radical, a 2,6-dimethoxyphenyl radical, α-substituted benzyl radicals, such as α-hydroxy-, α-amino-, α-carboxy-, α-sulfo-, or α-sulfonaminobenzyl radicals, a 2-or 3-thienylmethyl radical, an α-amino-2-thienylmethyl-or α-amino-3-thienylmethyl radical, an unsubstituted or substituted isoxazolyl radical, such as the 3-phenyl-5-methyl-4-isoxazolyl radical, or a 2-ethoxynaphthyl radical; that $R^2$ in particular can be a straight or branched chain lower aliphatic group, being optionally substituted with additional groups, such as the amino, guanidino, carboxy, carbalkoxy, carboxamido, hydroxy, mercapto, alkoxy or alkylthio groups, or with an aromatic or heterocyclic group, such as a phenyl, a mono- or di-hydroxyphenyl, an alkoxyphenyl, a halophenyl, an indolyl or an imidazolyl group, that $R^2$ further can be an unsubstituted or substituted aromatic or heterocyclic group, e.g. a phenyl or substituted phenyl group, or a pyridine or a thiophenone group; and that $R^3$, $R^4$, and $R^5$ in addition to hydrogen can also be the same or different straight or branched chain alkyl groups having from 1 to 6 carbon atoms, or that two of these substituents together with the nitrogen atom can form a ring which preferably contains from 5 to 8 ring atoms.

The salts of the compounds of the invention are preferably salts with pharmaceutically acceptable inorganic or organic acids such as hydrochloric acid, hydrobromic acid, sulfuric acid, phosphoric acid, tartaric acid, citric acid, fumaric acid, and the like.

If the ester moiety of the compounds of formula I contains an asymmetric carbon atom, the compounds exist in two diastereoisomeric forms, and the invention comprises the individual diastereoisomeric forms as well as mixtures thereof. The form in which the compounds are obtained depends on which of the enantiomers of the starting materials and which methods are used to make the compounds. The mixtures of the diastereoisomeric forms may be separated by fractional crystallization or other known methods.

It is well known that many penicillins, e.g. benzylpenicillin and a number of semisynthetic penicillins, are inefficiently or not at all absorbed from the gastrointestinal tract. Therefore, these penicillins must be given parenterally in order to obtain adequate serum levels. It is obvious that it will be advantageous to modify these penicillins in such a way that they will be absorbed efficiently when given orally, and at the same time retain their antibiotic activity.

It is one object of the present invention to provide new penicillin esters which possess advantageous properties as regards adequate absorption, distribution in the organism, and the like factors.

In contrast to many of the corresponding free penicillins, the compounds of the invention are efficiently absorbed from the gastrointestinal tract and are then, under the influence of enzymes, rapidly hydrolysed to the corresponding free penicillins. This hydrolysis is an important feature of the compounds of the invention. It is assumed that the first step consists in a hydrolysis to the hydroxymethyl esters of the corresponding penicillins which subsequently decompose spontaneously to the free penicillins.

According to experiments carried out in connection with the present invention it has been demonstrated in animal tests and in experiments in normal human volunteers that upon oral administration of the new penicillin esters of formula I, extremely high concentrations of the corresponding free penicillins are found in the blood and tissues due to efficient absorption combined with rapid hydrolysis in the organism. Experiments in normal human volunteers have further shown that the average amounts of benzylpenicillin excreted in the urine during 6 hours after oral administration of the varius aminoacyloxymethyl esters of benzylpenicillin are higher than those obtained after oral administration of equivalent doses of sodium benzylpenicillinate. Measurement of the peak blood levels of benzylpenicillin indicated a 2 to 6 fold increase in the case of the esters compared with sodium benzylpenicillinate.

The results of the experiments are given in the following Tables O and I showing mean serum levels and urinary excretions of benzylpenicillin, respectively, in normal volunteers following oral administration of 200 mg of benzylpenicillin sodium salt, called A, and chemically equivalent amounts of L-valyloxymethyl benzylpenicillinate, hydrochloride, called B, and L-1'-methoxy-4'-aspartoyloxymethyl benzylpenicillinate hydrochloride, called C.

Table 0

| Serum level in mcg/ml | | | | | |
|---|---|---|---|---|---|
| | Minutes after administration | | | | |
| Compound | 15 | 30 | 60 | 120 | 240 |
| A | 0.24 | 0.64 | 0.53 | 0.17 | 0 |
| B | 1.9 | 2.0 | 0.96 | 0.29 | 0.05 |
| C | 4.1 | 3.6 | 1.5 | 0.37 | 0.03 |

Table I

| Compound | Excretion of benzylpenicillin in percent of dose (0–6 hours) |
|---|---|
| A | 13.5 |
| B | 39.5 |
| C | 47.5 |

Under the same conditions, the urinary excretion of 2,6-dimethoxyphenylpenicillin (methicillin) following oral administration of 50 mg of sodium 2,6-dimethoxyphenylpenicillinate, and of chemically equivalent amounts of three aminoacyloxymethyl esters of methicillin was found to be as shown in Table II below.

Table II

| Compound | Excretion of methicillin in percent of dose (0–6 hours) |
|---|---|
| Methicillin, sodium salt | 2.9 |
| Methicillin, D,L-β-phenylglycyloxymethyl ester, HCl | 26.5 |
| Methicillin, L-valyloxymethyl ester, HCl | 28.5 |
| Methicillin, L-1'-methoxy-4'-aspartoyloxymethyl ester, HCl | 25.5 |

The nomenclature of the compounds of Tables 0 and I and II are in accordance with the rules of Internat. Union of Pure and Applied Chemistry (IUPAC).

Thus, the present penicillin esters are proposed in particular for oral administration in the treatment of patients suffering from infectious diseases which require a high concentration of the antibiotic in blood and tissues. In such cases, the desirable high concentration of the known penicillins has normally been obtained by administration by the parenteral route which is inconvenient to the patient, if the treatment is prolonged, and impractical for the medical practitioner.

The compounds of formula I are well tolerated compounds which are administered in clinical practice either as such, or preferably in the form of one of their salts, mixed with carriers and/or auxiliary agents and in any suitable form of pharmaceutical presentation for oral use.

In such compositions, the proportion of therapeutically active material to carrier substance and auxiliary agent can vary between 1 and 95%. The compositions can be worked up to pharmaceutical forms of presentation such as tablets, pills or dragees, or they can be filled into medical containers, such as capsules, or as far as suspensions are concerned, filled into bottles. Pharmaceutical organic or inorganic, solid or liquid carriers suitable for oral, enteral or parenteral administration can be used to make up the composition. Gelatine, lactose, starch, magnesium stearate, talc, vegetable and animal fats and oils, gums, polyalkylene glycols, and other known carriers for medicaments are all suitable as carriers. The preferred salts of the esters are the hydrochlorides, but salts with other inorganic or organic acids may be used, e.g. the hydrobromides, the hydroiodides, the sulfates, the phosphates, the tartrates, the maleates, the citrates, and the fumarates. Furthermore, the compositions may contain other pharmaceutically active components which can appropriately be administered together with the ester in the treatment of infectious diseases, such as other suitable antibiotics.

The compounds of the invention can be prepared by several methods among which the most interesting comprises reacting a salt of a penicillin of the general formula

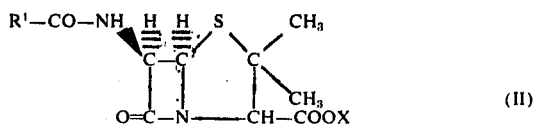

with a compound of the general formula $$Y - CH_2 - Cl \qquad (III)$$

in which formulae $R^1$ is as defined above, X is a cation such as $Na^+$, $K^+$, the ammonium or a trialkylammonium ion, and Y is bromine, iodine, an alkylsulphonyloxy or an arylsulphonyloxy radical, preferably in an inert organic solvent, e.g. dimethylformamide and at or below room temperature or at slightly elevated temperature, whereby a reaction product of the general formula IV is obtained:

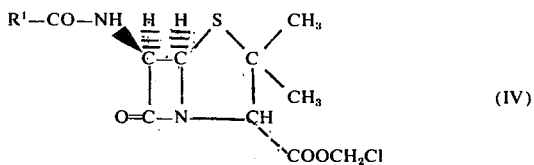

in which $R^1$ is as defined above. Hitherto chloromethyl esters have mainly been prepared by reacting acid halides with paraformaldehyde. However, this reaction is unsuitable when chemically labile reactants are involved as e.g. the penicillins possessing the vulnerable β-lactam ring. It has therefore been an essential improvement that we have found the above described procedure whereby a salt of an acid under very mild conditions can be converted to the corresponding chloromethyl ester.

The compounds of formula IV are new and interesting intermediates constituting as such a part of this invention.

In some cases the radical $R^1$ can have substituents which are affected by the reaction and which, therefore, must be protected during the reaction. This can be done in different ways well known to the man skilled in the art.

The compounds of formula IV are subsequently reacted with a salt, preferably an alkali metal salt, of a compound of the general formula

in which $R^2$, $R^5$, and $n$ have the meanings defined above and Z represents an unsubstituted or substituted amino group, a protected amino group, or a group which can be converted into an amino group, such as an azido group, a nitro group, or a halogen atom, preferably in an inert solvent at room temperature or at slightly elevated temperature whereby a compound of the formula VI is obtained:

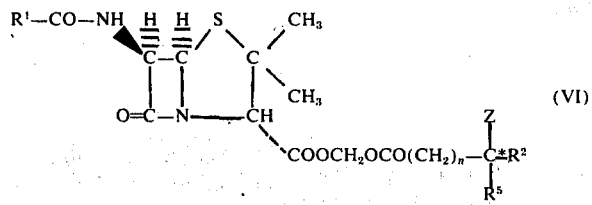

(VI)

in which $R^1$, $R^2 R^5$, Z and n are as defined above. When Z is an amino group or a substituted amino group, the reaction products of formula VI are identical with the compounds of the invention having formula I, and when Z has the other meanings defined above, the compounds of formula VI can be converted into the compounds of formula I, e.g. by hydrogenation or hydrolysis.

A common characteristic of the protecting groups of the substituent Z is that these are groups which can be split off by methods which are sufficiently mild to avoid cleavage of the molecule at the ester group or at the lactam ring. In particular, the protecting group of Z is a benzyloxycarbonyl radical, a p-halo-, p-nitro- or p-methoxy-benzyloxycarbonyl radical, $\beta,\beta,\beta$-trichloroethoxycarbonyl or an allyloxycarbonyl radical; or the protecting group is a sulphur-containing radical, such as a tritylsulphenyl radical, or an arylsulphenyl radical, e.g. an o-nitrophenylsulphenyl radical; the protecting group may also be a benzyl radical, a triphenylmethyl (also called trityl) radical, a tertiary butoxycarbonyl radical, or a radical obtained by reacting the free amino group with a $\beta$-dicarbonyl compound, such as acetylacetone, an acetoacetic ester, or benzoylacetone, to form an enamine or a Schiff base. In general, any group which can be split off by reduction, by mild acid hydrolysis, or by other mild reactions known per se will be suitable as protecting groups, since experiments have shown that the esters of formula I formed by the reaction in question are stable under such conditions.

The conversion of Z into an amino group can be effected by different procedures depending on what Z stands for. Catalytic hydrogenation will be preferred when Z stands for a benzylamino, dibenzylamino, or benzyloxycarbonylamino group and related groups, or for the tritylamino group. This hydrogenation is preferably performed at room temperature and at atmospheric or slightly elevated pressure in a solvent which is preferably a non-reducible organic solvent or a mixture thereof with water. The preferred catalyst is a noble metal catalyst, such as palladium or platinum, or Raney-Nickel, but other catalysts can be used as well. Electrolytic reduction can also be used in these cases. When Z stands for a $\beta,\beta,\beta$-trichloroethoxycarbonylamino group, reduction with zinc in acetic acid is preferred. A mild acid hydrolysis is preferred in the case where Z stands for a sulphur-containing group, an enamine or a Schiff base, for instance at a pH of about 2–4 in a diluted solution of hydrogen chloride, preferably in aqueous tetrahydrofuran. An acid hydrolysis, for instance with hydrochloric acid, acetic acid, p-toluenesulfonic acid or trifluoroacetic acid, can also be used for the elimination of the trityl and tert. butoxycarbonyl groups, and a treatment with formic acid at room temperature is especially suitable for the removal of the tert. butoxycarbonyl group. Also known from the literature is the removal of the o-nitrophenylsulphenyl group involving a nucleophilic attack on the sulphur atom of the sulphenamide group, the best yield in the present case being obtained with sodium or potassium iodide, sodium thiosulphate, sodium hydrogen sulphide, sodium dithionite or potassium thiocyanate. Other sulphenamide groups can be split in the same way. If Z is an azido group, a nitro group or a halogen atom, especially a bromine atom, it may be transformed into a free amino group in known manner, the azido and nitro groups by a catalytic hydrogenation with a noble metal catalyst, with Raney-Nickel, or by an electrolytic reduction, and the halogen atom by an amination, for instance with hexamethylenetetramine.

When one or more of the groups $R^1$ to $R^5$ contain a free hydroxy, mercapto, or amino group, these groups, if desired can be protected during the reaction by generally known methods, e.g. a hydroxy or mercapto group by etherification or acylation, an amino group by the above mentioned methods, and carboxylic groups, when present, by esterification.

In another embodiment of the method a compound of formula II is reacted with a compound of formula VII

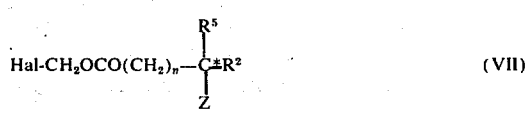

(VII)

in which Z, n, $R^2$, and $R^5$ are as defined above, and Hal stands for a halogen atom, preferably chlorine or bromine. The reaction is performed in an inert solvent below or at room temperature or at slightly elevated temperatures depending on the reactants and the solvent used. The reaction product has the formula VI above and, if necessary, e.g. when Z is different from

it can be converted into the compounds of formula I as already described above.

The compounds of formula VII are new compounds which can be prepared, for example, by reacting a salt of the acid of formula V with a compound of formula III in an inert solvent, such as acetone or dimethylformamide, or by reacting the acid chloride or bromide of the acids of formula V with paraformaldehyde in an inert solvent in a manner known per se.

The compounds of formula I can also be prepared by an acylation of compounds of formula VIIIa, or salts thereof, preferably hydrochlorides:

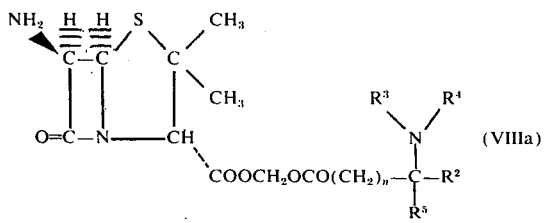

(VIIIa)

$R^2$ to $R^5$ and $n$ being as defined hereinbefore. The acylation is performed by reacting the compounds of formula VIIIa with reactive derivatives of the acids $R^1COOH$ in which $R^1$ is as defined hereinbefore. Reactive derivatives of the acids are for instance acid halides, acid anhydrides, mixed acid anhydrides of the acid $R^1COOH$ and preferably carbonic acid monoesters, acid azides, active esters, such as cyanomethyl esters, 2,4,5-trichlorophenyl esters, hydroxypiperidine esters, or active amides, such as acylimidazoles.

Furthermore the acid $R^1COOH$ as such can react with a compound of formula VIIIa in the presence of a carbodiimide, e.g. N,N'-dicyclohexylcarbodiimide, or an isoxazolium salt, e.g. N-ethyl-5-phenylisoxazolium-3'-sulfonate. The reaction conditions and the solvents used depend on the reactants and are obvious to any skilled person.

The compounds of the above formula VIIIa are new and can be prepared in different manners, for instance by reacting 6-aminopenicillanic acid with a compound of the formula

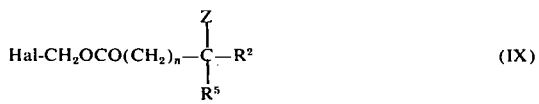

(IX)

in which $R^2$, $R^5$, Z, and $n$ are as defined above. The reaction is preferably performed in the presence of an amine, e.g. triethylamine, and at room temperature or slightly elevated temperatures in an inert solvent, such as dimethylformamide, whereby an intermediate of the formula

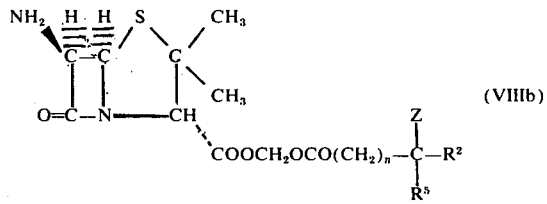

(VIIIb)

can be isolated which, after conversion of the group Z into an unsubstituted or substituted amino group, yields the compounds of formula VIIIa. The conversion of Z can be performed as described hereinbefore. The amino group at the 6-position of the penicillanic acid can be, but is not necessarily, protected by well-known protecting groups, for instance a trityl group.

The invention will not be illustrated by the following non-limiting Examples:

EXAMPLE 1

Glycycloxymethyl phenoxymethylpenicillinate

A. Chloromethyl phenoxymethylpenicillinate

To a solution of phenoxymethylpenicillin (70 g) and triethylamine (29.4 ml) in dimethylformamide (250 ml) was added chloroiodomethane (80 ml), and the mixture was stirred for 3.5 hours at room temperature. The mixture was then diluted with ethyl acetate (500 ml) and ether (500 ml) and filtered, and the filtrate was washed with water (3 × 250 ml), 0.5M aqueous sodium bicarbonate (100 ml), and water (2 × 100 ml). The organic phase was dried and evaporated in vacuo to yield the crude ester as a brownish gum, which could be used for the next step without further purification.

Dry column chromatography on silica gel of a sample of the crude ester yielded pure chloromethyl phenoxymethylpenicillinate as a slightly yellowish gum, which did not crystallize.

The nmr spectrum (CD$_3$OD) showed signals at $\delta$ = 1.52 (s), 1.60 (s), 4.57 (s), 4.63 (s), 5.65 (s), 5.88 (dd, j=8), and 6.90 –7.60 (m) ppm. TMS was used as internal reference.

B. Glycyloxymethyl phenoxymethylpenicillinate

Potassium N-[1-methyl-2-carbethoxy-vinyl]-glycinate hemihydrate, (3.51 g) (prepared as described in the specification to British Patent No. 986,904) was added to a solution of crude chloromethyl phenoxymethylpenicillinate (5.0 g), in dimethylformamide (75 ml), and the mixture was stirred for 20 hours at room temperature. The resulting brown solution was diluted with ethyl acetate (300 ml) and washed with water (3 × 75 ml), followed by 0.5M aqueous sodium bicarbonate (40 ml), and water (2 × 40 ml). After drying, the organic phase was evaporated in vacuo to yield crude N-[1-methyl-2-carbethoxy-vinyl]-glycyloxymethyl phenoxymethylpenicillinate as a brown oil. This material was dissolved in tetrahydrofuran (50 ml) without further purification, water (50 ml) was added, and the apparent pH-value of the mixture was adjusted to 2.5 by addition of 2N hydrochloric acid with stirring. During the hydrolysis, the pH-value was maintained by addition of further hydrochloric acid via an automatic titrator. When the consumption of acid has ceased, tetrahydrofuran was removed from the mixture at reduced pressure (bath-temperature about 35°C), and the remaining aqueous phase was extracted with ethyl acetate (2 × 15 ml). To the combined ethyl acetate extracts were added ether (30 ml) and water (50 ml), the pH-value of the aqueous phase was adjusted to 2.5 by addition of diluted hydrochloric acid while stirring, and the aqueous phase was separated. The combined aqueous phases were washed with ether (20 ml) and filtered, and the filtrate was freeze-dried to give the hydrochloride of the desired compound as a colourless amorphous product with a purity of 76%.

The nmr spectrum (CD$_3$OD) showed signals at δ = 1.52 (s), 1.60 (s), 3.98 (s), 4.58 (s), 4.65 (s), 5.63 (s), 5.98 (s), 6.80–7.60 (m) ppm. TMS was used as internal reference.

EXAMPLE 2

Alanyloxymethyl phenoxymethylpenicillinate

Potassium N-[1-methyl-2-carbethoxy-vinyl]-L-α-aminopropionate hemihydrate (1.86 g) was added to a solution of crude chloromethyl phenoxymethylpenicillinate (3.0 g) (prepared as described in Example 1A) in dimethylformamide (50 ml), and the mixture was stirred for 40 hours at room temperature. The resulting dark solution was worked up in the same way as described in Example 1B. An analogous acid hydrolysis of the resulting crude N-[1-methyl-2-carbethoxy-vinyl]-α-aminopropionyloxymethyl phenoxymethylpenicillinate and freeze-drying of the aqueous phase thus obtained gave the hydrochloride of the desired compound as an amorphous powder with a purity of 82%.

The potassium N-[1-methyl-2-carbethoxy-vinyl]-L-α-aminopropionate used in the above reaction was prepared in an analogous manner as described in the specification to British Patent No. 986,904 for the preparation of the corresponding D,L-compound, and obtained as a crystalline hemihydrate, m.p. 204.5–206°C, [α]$_D^{20}$+150° (c=0.5, CH$_3$OH).

EXAMPLE 3

α-Phenylglycyloxymethyl phenoxymethylpenicillinate

To a solution of crude chloromethyl phenoxymethylpenicillinate (20 g) (prepared as described in Example 1A) in dimethylformamide (300 ml) was added potassium N-[1-methyl-2-carbethoxy-vinyl]-D-α-amino-α-phenylacetate hemihydrate (%17.78 g) (prepared as described in Chem. Ber., 98, 789, (1965)), and the mixture was stirred for 20 hours at room temperature. After that, the cark solution was worked up to yield the crude N-[1-methyl-2-carbethoxy-vinyl]-α-phenylglycyloxymethyl phenoxymethylpenicillinate which was hydrolyzed in the same way as described in Example 1B. After removal of the tetrahydrofuran at reduced pressure, the remaining aqueous phase was extracted with ethyl acetate and freeze-dried to give the hydrochloride of the desired compound as a colourless amorphous powder with a purity of 88%. The nmr data given below indicate that a certain racemization had taken place during the reaction, and that consequently the reaction product was a mixture of the two epimeric forms.

The nmr spectrum (CD$_3$OD) showed signals at δ = 1.18, 1.23, 1.47, and 1.50 (4 s), 4.45 (s), 4.64 (s), 5.35 (s), 5.55 (dd, J=4) 5.75–6.20 (m), 6.80–7.50 (m), and 7.53 (s) ppm. TMS was used as internal reference.

EXAMPLE 4

β-Phenylalanyloxymethyl phenoxymethylpenicillinate

A. Potassium N-[1-methyl-2-carbomethoxy-vinyl]-L-α-amino-β-phenylpropionate hemihydrate was prepared in analogy to the preparation of the compounds described in British Patent No. 986,904. M.p. 158°–160°C.

B. 7.3 g of potassium N-[1-methyl-2-carbomethoxy-vinyl]-L-α-amino-β-phenylpropionate hemihydrate were added to a solution of crude chloromethyl phenoxymethylpenicillinate (8.0 g) in 100 ml dimethylformamide (DMF), and the mixture was stirred at room temperature for 20 hours. The resulting dark solution was worked up in the same way as described in Example 1B. A similar acid hydrolysis of the resulting crude N-[1-methyl-2-carbomethoxy-vinyl]-α-amino-β-phenylpropionyloxymethyl phenoxymethylpenicillinate and freeze-drying of the aqueous phase thus obtained gave the hydrochloride of the desired compound as an amorphous powder with a purity of 71%.

The ir spectrum showed strong bands at 1785–1760 (b) and 1685 cm$^{-1}$. Thin layer chromatography (TLC) on silica gel HF$_{254}$ (Merck) showed a single spot with R$_f$ = 0.63 (solvent system: n-butanol-acetic acid-H$_2$O, 4:1:5).

EXAMPLE 5

β-Alanyloxymethyl phenoxymethylpenicillinate

This compound was prepared analogously to the compound described in Example 1B from potassium N-[1-methyl-2-carbomethoxy-vinyl]-β-aminopropionate (mp. 228°–230°C) and chloromethyl phenoxymethylpenicillinate. The hydrochloride of the desired compound was obtained as an amorphous powder with a purity of 69%. TLC:R$_f$ = 0.43. (Solvent system: n-butanol-acetic acid-H$_2$O, 4:1:5).

EXAMPLE 6

Glycyloxymethyl phenoxymethylpenicillinate

A. N-Tritylglycine chloromethyl ester

To a solution of N-tritylglycine (25.6 g) and triethylamine (14.0 ml) in dimethylformamide (DMF) (60 ml), a solution of chloroiodomethane (24.0 ml) in DMF (40 ml) was added dropwise while stirring, and the mixture was stirred for 3.5 hours at room temperature. Then the mixture was poured into water (400 ml), the organic phase was separated, and the aqueous phase was extracted with ethyl acetate. The combined organic phases were washed with water and thereafter twice with aqueous sodium bicarbonate and again with water. The organic phase was dried and evaporated in vacuo to yield the crude ester. TLC: R$_f$ = 0.7 (cyclohexane-ethyl acetate, 1:1), ir )CHCl$_3$): 1765 cm$^{-1}$ (ester carbonyl), nmr (CDCl$_3$-TMS standard): δ = 3.20 (s), 5.53 (s), 7.00–7.30 (m) ppm.

B. N-Tritylglycyloxymethyl phenoxymethylpenicillinate

To a solution of N-tritylglycine chloromethyl ester (7.1 g) in DMF (90 ml) was added potassium phenoxymethylpenicillinate (8.0 g) and potassium iodide (0.1 g), and the suspension was stirred for 7 days. The mixture was then diluted with ethyl acetate and filtered, and the filtrate was washed with aqueous sodium bicarbonate and water. The organic phase was dried and evaporated in vacuo.

The crude material thus obtained was purified by dry column chromatography on silica gel (eluent: cyclohexaneethyl acetate, 7:3) to afford the pure compound as a slightly yellowish gum.

TLC: R$_f$ = 0.49 (cyclohexane-ethyl acetate, 1:1), ir (CHCl$_3$): 1760–1790 cm$^{-1}$ (broad), 1730 cm$^{-1}$, 1695 cm$^{-1}$, nmr (CDCl$_3$-TMS standard): δ = 1.42 (s), 1.55

(s), 3.20 (s), 4.45 (s), 4.55 (s), 5.50–5.90 (m), 5.73 (s), 6.80–7.70 (m) ppm.

C. Glycyloxymethyl phenoxymethylpenicillinate

To a solution of N-tritylglycyloxymethyl phenoxymethylpenicillinate (400 mg) in dioxane (5ml) was added water (2.5 ml), and the apparent pH-value of the mixture was adjusted to 2 by addition of 0.2N hydrochloric acid while stirring. After stirring for 1 hour at room temperature, water (15 ml) was added, and the mixture was extracted with ethyl acetate (2 × 5 ml). The remaining aqueous phase was freeze-dried to give a slightly yellowish powder which was identical with the compound described in Example 1B.

EXAMPLE 7

Glycyloxymethyl phenoxymethylpenicillinate

A. N-Tert.butoxycarbonyl-glycine chloromethyl ester

To a solution of chloroiodomethane (8.0 ml) in DMF (10 ml), a solution of N-tert.butoxycarbonyl-glycine and triethylamine (4 ml) in DMF (10 ml) was added dropwise while stirring, and the mixture was further stirred for 2.5 hours. The resulting solution was worked up in the same way as described in Example 6A.

After purification by dry column chromatography on silica gel (eluent: cyclohexane-ethyl acetate, 7:3) the pure compound was obtained as a gum.

TLC: $R_f$ = 0.55 (cyclohexane-ethyl acetate, 1:1), ir (CHCl$_3$): 1773 cm$^{-1}$, 1710 cm$^{-1}$.

B. N-Tert.butoxycarbonylglycyloxymethyl phenoxymethylpenicillinate

A suspension of N-tert.butoxycarbonyl-glycine chloromethyl ester (0.7 g), potassium phenoxymethylpenicillinate (1.3 g), and potassium iodide (0.1 g) in DMF (15 ml) was stirred for 10 days at room temperature. The resulting mixture was worked up in the same way as described in Example 6B. The crude compound thus obtained could be used in the next step without further purification.

TLC: $R_f$ = 0.24 (cyclohexane-ethyl acetate, 1:1), ir (CHCl$_3$): 1775–1790 cm$^{-1}$ (broad, 1690–1720 cm$^{-1}$ broad), nmr (CDCl$_3$-TMS standard): δ = 1.46 (s), 1.51 (s), 1.60 (s), 3.97 (d,J=6), 4.50 (s), 4.57 (s), 5.50–5.80 (m), 5.08 (t,J=6), 5.87 (ABq,J=6), and 6.80–7.50 (m) ppm.

C. Glycyloxymethyl phenoxymethylpenicillinate

Acid hydrolysis of 650 mg of the protected ester of step B in a similar manner as described in Example 6C yielded an amorphous product which was identical with the compound prepared in Example 1B.

EXAMPLE 8

Glycyloxymethyl phenoxymethylpenicillinate

A. N-Carbobenzoxy-glycine chloromethyl ester

A solution of N-carbobenzoxy-glycine (4.2 g), chloroiodomethane (6.0 ml), and triethylamine (3.5 ml) in DMF (10 ml) was stirred for 2 hours at room temperature. The mixture was worked up and purified in the same way as described in Example 6A to yield the desired compound as a slightly yellowish oil.

TLC: $R_f$ = 0.48 (cyclohexane-ethyl acetate, 1:1), ir (CHCl$_3$): 1775 cm$^{-1}$, 1720 cm$^{-1}$, nmr (CDCl$_3$-TMS standard): δ = 4.00 (bd,J=5), 5.13 (s), 5.60 (bt), 5.72 (s), and 7.34 (s) ppm.

B. N-Carbobenzoxyglycyloxymethyl phenoxymethylpenicillinate

A suspension of N-carbobenzoxy-glycine chloromethyl ester (3.4 g), potassium phenoxymethylpenicillinate (5.0 g), and potassium iodide (0.2 g) in DMF (75 ml) was stirred for 12 days at room temperature. This mixture was worked up in the same way as described in Example 6B. The desired compound was obtained as a slightly yellowish gum.

TLC: $R_f$ = 0.24 (cyclohexane-ethyl acetate, 1:1), nmr (CDCl$_3$-TMS standard): δ = 1.48 (s), 1.57 (s), 3.02 (d,J=6), 4.48 (s), 4.57 (s), 5.15 (s), 5.30 (broad), 5.50–5.80 (m), 5.88 (ABq,J=6), 6.80–7.50 (m), and 7.38 (s) ppm.

C. Glycyloxymethyl phenoxymethylpenicillinate

Removal of the carbobenzoxy protecting group was effected by catalytic hydrogenation of the protected ester in tetrahydrofuran-water 1:1 at pH 2.5, 10% palladium on carbon being used as a catalyst. Removal of tetrahydrofuran at reduced pressured followed by freeze-drying of the remaining aqueous phase gave an amorphous product which was identical with the compound described in Example 1B.

EXAMPLE 9

β-Phenylalanyloxymethyl phenoxymethylpenicillinate

A. N-Tert.butoxycarbonyl-β-phenylalanine chloromethyl ester

This compound was prepared by the method of Example 7A from N-tert.butoxycarbonyl-β-phenylalanine (11.0 g), triethylamine (3.7 ml), and chloroiodomethane (16.5 ml) in DMF (75 ml), reaction time 4 hours.

TLC: $R_f$ = 0.70 (cyclohexane-ethyl acetate, 1:1), nmr (CDCl$_3$-TMS standard): δ = 1.43 (s), 3.10 (m), 4.70 (m), 5.67 (d,J=6), 5.82 (d,J=6), 7.0–7.5 (m) ppm.

B. N-Tert.butoxycarbonyl-β-phenylalanyloxymethyl phenoxymethylpenicillinate

The compound was prepared by the method of Example 7B from N-tert.butoxycarbonyl-β-phenylalanine chloromethyl ester and potassium phenoxymethylpenicillinate; reaction time 5 days.

TLC: $R_f$ = 0.45 (cyclohexane-ethyl acetate, 1:1), nmr (CDCl$_3$-TMS standard): δ = 1.42 (s), 1.50 (s), 1.58 (s), 3.08 (m), 4.50 (s), 4.57 (s), 4.85 (m), 5.50–5.80 (m), 5.80 (d,J=5), 5.92 (d,J=5), and 6.80–7.60 (m) ppm.

C. β-Phenylalanyloxymethyl phenoxymethylpenicillinate

The N-tert.butoxycarbonyl group was removed under essentially the same conditions as described in Example 6C, yielding a compound identical to that of Example 4.

EXAMPLE 10

Prolyloxymethyl phenoxymethylpenicillinate

A. N-Tert.butoxycarbonyl-proline chloromethyl ester

The compound was prepared by the method of Example 7A from N-tert.butoxycarbonyl-proline, triethylamine, and chloroiodomethane in dimethylformamide; reaction time four hours.

TLC: $R_f$ = 0.53 (cyclohexane-ethyl acetate, 1:1), nmr (CDCl$_3$-TMS standard): δ = 2.05 (m), 3.50 (m), 4.33 (m), and 5.77 (bs) ppm.

B. N-Tert.butoxycarbonyl-prolyloxymethyl phenoxymethylpenicillinate

The compound was prepared by the method of Example 7B from N-tert.butoxycarbonyl-proline chloromethyl ester and potassium phenoxymethylpenicillinate; reaction time 3 days.

TLC: $R_f = 0.28$ (cyclohexane-ethyl acetate, 1:1), ir (CHCl$_3$): 1760–1790 cm$^{-1}$, 1690 cm$^{-1}$, nmr (CDCl$_3$-TMS standard): $\delta = 1.45$ (s), 1.53 (s), 1.60 (s), 2.00 (m), 3.50 (m), 4.30 (m), 4.50 (s), 4.57 (s), 5.50–5.80 (m), 5.80 (d,J=5), 5.95 (d,J=5), and 6.80–7.60 (m) ppm.

C. Prolyloxymethyl phenoxymethylpenicillinate

By following the procedure of Example 7C and substituting the tert.butoxycarbonyl-prolin derivative for the tert.butoxycarbonyl-glycine derivative, the hydrochloride of prolyloxymethyl phenoxymethylpenicillinate was obtained.

EXAMPLE 11

Tryptophyloxymethyl phenoxymethylpenicillinate

A. N-Tert.butoxycarbonyl-tryptophan chloromethyl ester

The compound was prepared by the method of Example 7A from N-tert.butoxycarbonyl-tryptophan, triethylamine, and chloroiodomethane in dimethylformamide; reaction time 4 hours. M.p. 155°–157°C.

B. N-Tert.butoxycarbonyl-tryptophyloxymethyl phenoxymethylpenicillinate

The compound was prepared by the method of Example 7B from N-tert.butoxycarbonyl-tryptophan, chloromethyl ester, and potassium phenoxymethylpenicillinate; reaction time 6 days.

TLC: $R_f = 0.3$ (cyclohexane-ethyl acetate, 1:1), nmr (CDCl$_3$-TMS standard): $\delta = 1.42$ (s), 1.45 (s), 1.55 (s), 3.30 (d,J=6), 4.43 (s), 4.57 (s), 5.00 (s), 5.50–5.90 (m), 5.80 (ABq,J=6), and 6.80–7.70 (m) ppm.

C. Tryptophyloxymethyl phenoxymethylpenicillinate

By following the procedure of Example 7C and substituting the tert.butoxycarbonyl-tryptophyloxymethyl derivative for the tert.butoxy-carbonyl glycine derivative, the hydrochloride of tryptophyloxymethyl-phenoxymethylpenicillinate was obtained.

EXAMPLE 12

Glycine chloromethyl ester p-toluenesulphonate 3.5 g of N-tritylglycine chloromethyl ester in acetone (25 ml) were treated with p-toluenesulphonic acid (1.9 g) in acetone (25 ml). After standing for one-half hour at room temperature, the resulting precipitate was collected on a filter. The product thus obtained had a melting point of 188°–190°C.

By substituting glycine chloromethyl ester p-toluenesulphonate for the tritylglycine chloromethyl ester in Example 6B, glycyloxymethyl phenoxymethylpenicillinate was directly obtained.

EXAMPLE 13

β-Phenylalanyloxymethyl phenoxymethylpenicillinate

A. β-Phenylalanine chloromethyl ester, hydrobromide 4.2 g of N-tert.butoxycarbonyl-β-phenylalanine chloromethyl ester were treated with HBr in acetic acid (5 ml) at room temperature. A precipitate formed immediately and, after a few minutes, the reaction mixture was filtered to give a product with a melting point of 188°–190°C.

By substituting N-tert.butoxycarbonyl-D,L-valine chloromethyl ester for the above ester, the D,L-valine chloromethyl ester, hydrobromide was obtained with a m.p. of 132°–134°C.

B. β-Phenylalanyloxymethyl phenoxymethylpenicillinate

By substituting the β-phenylalanine chloromethyl ester, hydrobromide for the N-tert.butoxycarbonyl-glycine chloromethyl ester and following the procedure of Example 7B, β-phenylalanyloxymethyl phenoxymethylpenicillinate was directly obtained.

EXAMPLE 14

α-Phenylglycyloxymethyl benzylpenicillinate

A. Chloromethyl benzylpenicillinate

To a suspension of triethylammonium benzylpenicillinate (44 g) in DMF (400 ml) was added chloroiodomethane (40 ml). After stirring overnight, the mixture was diluted with ethyl acetate (1200 ml) and extracted with water (2 × 400 ml), 2% aqueous sodium bicarbonate (100 ml), and finally water (2 × 200 ml). The organic phase was dried and filtered, and the filtrate was evaporated in vacuo to give chloromethyl benzylpenicillinate as a dark, viscous oil.

The crude material was purified by dry column chromatography on silica gel (cyclohexane-ethyl acetate 7:3), and the pure chloromethyl benzylpenicillinate thus obtained was crystallized from ether:petroleum ether to yield colourless crystals with m.p. 92°–93°C.

$[\alpha]_D^{20} = +179.8°$ (c=1, CHCl$_3$) The ir-spectrum (KBr) showed strong bands at: 1785, 1770, 1655, 1547, 1303, 1139, 1118, and 712 cm$^{-1}$. The nmr-spectrum (CDCl$_3$) showed signals at $\delta = 1.51$ (s), 3.64 (s), 4.41 (s), 5.53 (d,J=5), 5.68 (dd,J=5, J=9), 5.69 (d,J=6), 5.85 (d,J=6), 6.2 (d,J=8–9), and 7.35 (s) ppm. TMS was used as internal reference.

B. α-Phenylglycyloxymethyl benzylpenicillinate

To a solution of chloromethyl benzylpenicillinate (9.6 g) in dimethylformamide (150 ml) was added potassium N-[1-methyl-2-carbomethoxy-vinyl]-D-α-amino-α-phenylacetate, hemihydrate (8.9 g).

After stirring for 16 hours at room temperature, the mixture was diluted wih ethyl acetate (600 ml) and extracted with water (2 × 150 ml), 1% aqueous sodium bicarbonate (75 ml), and water (150 ml).

The organic phase was dried, filtered, and evaporated in vacuo. The oily residue thus obtained was taken up in tetrahydrofuran (100 ml), water (80 ml) was added, and the apparent pH-value of the stirred mixture was adjusted to 2.5 by addition of 1N hydrochloric acid. During the hydrolysis, this pH was maintained by addition of further hydrochloric acid via an automatic titrator. When the consumption of acid had ceased, the tetrahydrofuran was removed from the mixture at reduced pressure. The remaining phase was washed with ethyl acetate (2 × 25 ml) and freeze-dried to give the hydrochloride of the desired compound as a colourless, amorphous powder with a purity of 88%.

EXAMPLE 15

L-Valyloxymethyl benzylpenicillinate hydrochloride

To a solution of chloromethyl benzylpenicillinate (38.0 g) in dimethylformamide (300 ml) was added N-[1-methyl-2-carbomethyl-vinyl].L-valine potassium salt (30.0 g).

After stirring for 20 hours at room temperature, the mixture was diluted with ethyl acetate (1 liter) and extracted with water (2 × 300 ml), 1% aqueous sodium bicarbonate (300 ml), and water (300 ml).

The organic phase was dried, filtered, and evaporated in vacuo. The oily residue thus obtained was taken up in tetrahydrofuran (300 ml), water (200 ml) was added, and the apparent pH-value of the stirred mixture was adjusted to 2.5 by addition of 4N hydrochloric acid. During the hydrolysis, this pH was maintained by addition of further hydrochloric acid. When the consumption of acid had ceased, the tetrahydrofuran was removed from the mixture at reduced pressure. The remaining aqueous phase was washed with ethyl acetate (2 × 100 ml) and freeze-dried. The residue was triturated with n-butanol (80 ml), and the separated solid was filtered off, washed with n-butanol and ether, and dried to give colourless crystals with a melting point of 121°–123°C (dec.).

By substituting N-[1-methyl-2-carbomethoxy-vinyl]-D-valine potassium salt for the corresponding L-isomer used above, the hydrochloride of D-valyl-oxymethyl benzylpenicillinate was obtained, and by substituting the D,L-isomer for the L-isomer used above, the hydrochloride of D,L-valyloxymethyl benzylpenicillinate was obtained.

EXAMPLE 16

L-β-Phenylalanyloxymethyl benzylpenicillinate, hydrochloride 8.08 g of potassium N-[1-methyl-2-carbomethoxy-vinyl]-L-α-amino-β-phenylpropionate, hemihydrate were added to a solution of 8.0 g of crude chlormethyl benzylpenicillinate in dimethylformamide (100 ml), and the mixture was stirred at room temperature for 16 hours. The resulting dark solution was worked up in the same way as described in Example 14B. A similar acid hydrolysis of the resulting crude N-[1-methyl-2-carbomethoxy-vinyl]-L-α-amino-β-phenylpropionyloxymethyl benzylpenicillinate and freeze-drying of the aqueous phase thus obtained gave the desired compound as an amorphous powder, which crystallized from n-butanol; m.p. 130°–131°C (dec.); $[\alpha]_D^{20} + 192°$ (c=0.5); ethanol.

By substituting potassium N-[1-methyl-2-carbomethoxy-vinyl]-D-α-amino-β-phenylpropionate, hemihydrate for the corresponding L-isomer, the hydrochloride of D-β-phenylalanyloxymethyl benzylpenicillinate was obtained as an amorphous powder with a purity of 84%. Its nmr spectrum ($CD_3OD$) showed signals at δ = 1.50 (s), 1.63 (s), 3.25 (d,J=7), 3.63 (s), 4.47 (t,J=7), 4.53 (s), 5.55 (s), 5.97 (s), 7.33 (s), and 7.37 (s) ppm. TMS was used as internal reference.

EXAMPLES 17–23

By following the procedure described in Example 15 and substituting the salts listed in the Table 2 below for the N-[1-methyl-2-carbomethoxy-vinyl]-L-valine potassium salt, the aminoacyloxymethyl benzylpenicillinates listed in Table 1 were obtained as amorphous hydrochlorides.

The compounds of Tables 1 and 2 are of the general formula

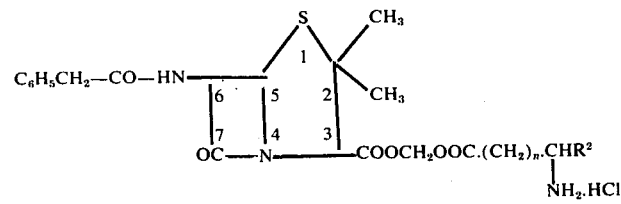

Table 1

| Example | n | R² | Purity % (iodometric assay) | TLC R_f 1) 2)* |
|---|---|---|---|---|
| 17 | 0 | —CH₂CH(CH₃)CH₃ | 79 | 1) 0.70  2) 0.50 |
| 18 | 0 | —CH(CH₃)CH₃ | 86 | 1) 0.63  2) 0.61 |
| 19 | 0 | —C(CH₃)₃ | 83 | 1) 0.73  2) 0.55 |
| 20 | 0 | —CH₂COOCH₃ | 88 | 1) 0.43  2) 0.68 |
| 21 | 1 | —COOCH₃ | 92 | 1) 0.48  2) 0.51 |
| 22 | 0 | H | 81 | |
| 23 | 0 | —CH₂CH₂SCH₃ | 92 | 2) 0.60 |

*1) Solvent system: (n-butanol-ethanol-$H_2O$; 8:2:2)
 2) — — : (n-butanol-acetic acid-$H_2O$; 4:1:5)

The compounds of Table 1 were characterized by the nmr spectra listed below:

nmr ($CH_3OD$ - TMS standard)

| Ex. | 2 CH₃ | 3H | 5H+6H | C₆H₅CH₂CO | ⟨O⟩ | OCH₂O | —CHNH₂HCl | |
|---|---|---|---|---|---|---|---|---|
| 17 | 1.52(s) 1.64(s) | 4.53(s) | 5.55(s) | 3.63(s) | 7.33(s) | 5.92(d) 6.08(d) ABq J=— | 4.1(m) | —CH₂CH(CH₃)CH₃  1.0(m),1.7(m) |
| 18 | 1.54(s) 1.66(s) | 4.55(s) | 5.58(s) | 3.66(s) | 7.35(s) | 5.94(d) 6.13(d) ABq J=6 | 4.16(d) J=4 | —CH(CH₃)C₂H₅  1.07(d)J=7.20(m) 1.0(m),1.4(m) |
| 19 | 1.53(s) 1.64(s) | 4.53(s) | 5.55(s) | 3.63(s) | 7.32(s) | 5.93(d) 6.10(d) ABq J=6 | 3.92(s) | —C(CH₃)₃  1.13(s) |
| 20 | 1.50(s) 1.63(s) | 4.52(s) | 5.54(s) | 3.63(s) | 7.30(s) | 5.88(d) 6.03(d) ABq J=6 | 4.50(t) J=5 | —CH₂COOCH₃  3.75(s),3.10(d) J=5 |
| 21 | 1.52(s) 1.64(s) | 4.53(s) | 5.57(s) | 3.64(s) | 7.33(s) | 5.93(s) | 4.47(t) J=5.5 | —CH₂— 3.18(d) J=5.5 COOCH₃ |

-continued
nmr (CH₃OD - TMS standard)

| Ex. | 2 CH$_3$ | 3H | 5H+6H | C$_6$H$_5$CH$_2$CO | | OCH$_2$O | —CHNH$_2$HCl |
|---|---|---|---|---|---|---|---|
| 22 | 1.52(s)<br>1.65(s) | 4.53(s) | 5.55(s) | 3.63(s) | 7.32(s) | 5.98(s) | 3.97(s)<br>3.87(s) |
| 23 | 1.52(s)<br>1.63(s) | 4.52(s) | 5.53(s) | 3.62(s) | 7.29(s) | 5.93(d)<br>6.03(d)<br>ABq J=5 | 4.32(t)<br>J=6 | —CH$_2$CH$_2$SCH$_3$<br>2.11(s)<br>2.20(m)<br>2.68(m) |

The starting materials used in Examples 14-23, which are potassium salts of N-[1-methyl-2-carbomethoxyvinyl]amino acids, were prepared according to the procedure described in British Pat. No. 986,904, in Example 1, and in Chem.Ber. 98, 789 (1965), and have the formula

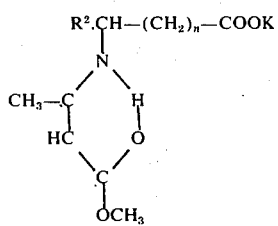

Table 2

| Amino Acid | R$^2$ | n | M.p. in °C |
|---|---|---|---|
| 1. L-valine | (CH$_3$)$_2$CH— | 0 | 216–218 |
| 2. D-valine | — | 0 | — |
| 3. D,L-veline | — | 0 | — |
| 4. L-leucine | (CH$_3$)$_2$.CH.CH$_2$— | 0 | 214–216 |
| 5. L-isoleucine | C$_2$H$_5$.CH.CH$_3$ | 0 | 246–248 |
| 6. D,L-tert.leucine | (CH$_3$)$_3$C— | 0 | 143–145 |
| 7. L-aspartic acid α-methyl ester* | —COOCH$_3$ | 1 | 184–186 |
| 8. L-aspartic acid β-methyl ester** | —CH$_2$COOCH$_3$ | 0 | 112–114 |
| 9. Glycine | H— | 0 | 233–234 |
| 10. D-α-phenylglycine | C$_6$H$_5$— | 0 | 240–241 |
| 11. L-methionine | CH$_3$S—CH$_2$.CH$_2$ | 0 | 160–162 |

*J.Am.Chem.Soc. 85, 1844 (1963)
**J.Am.Chem.Soc. 79, 5701 (1957)

EXAMPLE 24

A. α-Azido-α-methylpropionyloxymethyl benzylpenicillinate

To a solution of chloromethyl benzylpenicillinate (3.8 g) in dimethylformamide (50 ml) were added sodium α-azido-α-methylpropionate (1.6 g) and sodium iodide (50 mg), and the mixture was stirred for 24 hours at room temperature.

Then the mixture was diluted with ethyl acetate and washed with water, aqueous sodium bicarbonate, and finally water. The organic phase was dried (MgSO$_4$), filtered and evaporated in vacuo to give a sightly yellowish crystalline product. Trituration of this product with isopropanol gave a solid with m.p. 87°–89°C.

B. α-Amino-α-methylpropionyloxymethyl benzylpenicillinate hydrochloride

A solution of α-azido-α-methylpropionyloxymethyl benzylpenicillinate (1.43 g) in tetrahydrofuran (30 ml) was placed in a three-necked flask equipped with a gas inlet-outlet tube, a glass-calomel combination electrode, a burette, and a magnetic stirrer. Water (20 ml) and 10% palladium-on-carbon catalyst (1.0 g) were added. The system was flushed with nitrogen, after which a stream of hydrogen was bubbled through the suspension while stirring, a pH-value of 3–4 being maintained in the suspension by the addition of 0.5N hydrochloric acid (3.4 ml). When the consumption of acid had ceased, the catalyst was filtered off. Tetrahydrofuran was removed from the mixture at reduced pressure (bath-temperature about 35°C), and the remaining aqueous phase was extracted with ethyl acetate. The aqueous phase was separated and freeze-dried to give the desired compound as a colourless amorphous powder with a purity of 87% (iodometric).

TLC: R$_f$ = 0.54 (n-butanol-acetic acid-H$_2$O; 4:1:5). The nmr spectrum (CD$_3$OD) showed peaks at δ = 1.50 (s), 1.60 (s), 3.63 (s), 4.53 (s), 5.53 (s), 5.98 (s), 7.30 (s) ppm., TMS being used as internal reference.

EXAMPLE 25

D,L-Valyloxymethyl benzylpenicillinate

A. N-tert.butoxycarbonyl-D,L-valine chloromethyl ester

This compound was prepared by the method of Example 7A from tert.butoxycarbonyl-D,L-valine (2.2 g), triethylamine (2.0 ml), and chloroiodomethane (4.0 ml) in DMF (10 ml); reaction time 3 hours.

TLC: R$_f$ = 0.68 (cyclohexane-ethyl acetate, 1:1); nmr (CDCl$_3$-TMS standard): δ: 0.95 (d,J=6.5), 1.00 (d,J=6.5), 1.45 (s), 4.27 (dd,J=5 and J=9), 5.00 (bd), 5.67 (d,J=6), 5.91 (d,J=6).

B. N-tert.butoxycarbonyl-D,L-valyloxymethyl benzylpenicillinate

This compound was prepared analogously to the compound described in Example 7B from the potassium salt of benzylpenicillinate and N-tert.butoxycarbonyl-D,L-valine chloromethyl ester.

C. D,L-valyloxymethyl benzylpenicillinate hydrochloride

The N-tert.butoxycarbonyl group was removed under essentially the same conditions as described in Example 6C, yielding a compound identical with that mentioned in Example 15.

EXAMPLE 26

α-Phenylglycyloxymethyl 2,6-dimethoxyphenylpenicillinate

A. Chloromethyl 2,6-dimethoxyphenylpenicillinate

To a suspension of sodium 2,6-dimethoxyphenylpenicillinate, monohydrate (10.51 g) in dimethylformamide (50 ml) was added chloroiodomethane (10 ml), and the mixture was stirred for 3.5 hours at room temperature. After dilution with ethyl acetate (100 ml) and ether (100 ml), the mixture was washed with water (3 × 50 ml), 0.5M aqueous sodium bicarbonate (25 ml), and water (2 × 25 ml) to remove the greater part of dimethylformamide and unreacted penicillin salt. The organic phase was dried and evaporated in vacuo to give the crude ester as a yellowish gum. This material could be used in the next step without further purification. A sample of the crude ester was purified by dry column chromatography on silica gel and gave pure chloromethyl 2,6-dimethoxyphenylpenicillinate as a slightly yellowish gum, which did not crystallize.

The nmr spectrum (CDCl$_3$) showed signals at $\delta =$ 1.57 (s), 1.68 (s), 3.83 (s), 4.45 (s), 5.80 (dd,J=7), 5.80 (m), 6.62 (d,J=7), and 7.34 (t,J=7) ppm.

TMS was used as internal reference.

B. α-Phenylglycyloxymethyl 2,6-dimethoxyphenylpenicillinate

To a solution of crude chloromethyl 2,6-dimethoxyphenylpenicillinate (4.28 g) in dimethylformamide (60 ml) was added potassium N-[1-methyl-2-carbethoxy-vinyl]-D-α-amino-α-phenylacetate, hemihydrate (3.72 g), and the mixture was stirred for 18 hours at room temperature. The resulting yellow solution was diluted with ethyl acetate (240 ml) and washed with water (3 × 60 ml), followed by 0.5N aqueous sodium bicarbonate (30 ml), and water (2 × 20 ml). After drying, the organic phase was evaporated in vacuo to give crude N-[1-methyl-2-carbethoxy-vinyl]-α-phenylglycyloxymethyl 2,6-dimethoxyphenylpenicillinate as a yellow oil. This material was hydrolyzed in the same way as described in Example 1B. When the reaction was finished, tetrahydrofuran was removed from the mixture at reduced pressure, and the remaining aqueous phase was extracted with ethyl acetate and freeze-dried to give the hydrochloride of the desired compound as a colourless amorphous powder with a purity of 90%. The nmr data given below indicate that a certain racemization has taken place during the reaction, and that the reaction product consequently is a mixture of the two epimeric forms. The nmr spectrum (CD$_3$OD) showed signals at $\delta =$ 0.97, 1.12, 1.43, and 1.52 (4s), 3.80 (s), 4.65 (s), 5.32, (s), about 5.95 (bs), 6.72 (d,J=8), 7.40 (m), and 7.52 (s) ppm.

TMS was used as internal reference.

EXAMPLE 27

L-β-Phenylalanyloxymethyl 2,6-dimethoxyphenylpenicillinate, hydrochloride

To a solution of crude chloromethyl 2,6-dimethoxyphenylpenicillinate (11.8 g) in dimethylformamide (150 ml) was added potassium N-[1-methyl-2-carbomethoxy-vinyl]-L-α-amino-β-phenylpropionate, hemihydrate (10.68 g), and the mixture was stirred for 16 hours at room temperature. The resulting yellow solution was diluted with ethyl acetate (600 ml) and washed with water (3 × 150 ml), followed by 0.5M aqueous sodium bicarbonate (75 ml), and water (2 × 75 ml). After drying, the organic phase was evaporated in vacuo to give crude N-[1-methyl-2-carbomethoxy-vinyl]-L-β-phenylalanyloxymethyl 2,6-dimethoxyphenylpenicillinate as a yellow oil. This material was hydrolyzed in the same way as described in Example 1B. When the reaction was finished, tetrahydrofuran was removed from the mixture at reduced pressure, and the remaining aqueous phase was extracted with ethyl acetate and freee-dried to give the desired compound as a colourless amorphous powder with a purity of 89%.

The nmr spectrum (CD$_3$OD) showed signals at $\delta =$ 1.52 (s), 1.67 (s), 3.25 (d,J=7), 3.80 (s), 4.49 (s), 4.57 (bt,J=7), 5.69 (d,J=4.5), 5.77 (d,J=4.5), 5.95 (bs), 6.68 (d,J=8), 7.30 (t,J=8), and 7.35 (s) ppm.

TMS was used as internal reference.

EXAMPLE 28

L-Valyloxymethyl 2,6-dimethoxyphenylpenicillinate, hydrochloride 3.04 g of the potassium salt of N-[1-methyl-2-carbomethoxy-vinyl]-L-valine were added to a solution of 4.28 g of chloromethyl 2,6-dimethoxyphenylpenicillinate in dimethylformamide (60 ml), and the mixture was stirred at room temperature for 16 hours. The resulting yellow solution was worked up in the same way as described in Example 1B. A similar acid hydrolysis of the resulting crude N-[1-methyl-2-carbomethoxy-vinyl]-L-valyloxymethyl 2,6-dimethoxyphenylpenicillinate and freeze-drying of the aqueous phase thus obtained gave the desired compound as a colourless amorphous product with a purity of 88%.

The nmr spectrum (CD$_3$OD) showed signals at $\delta =$ 1.09 (d,J=6.5), 1.54 (s), 1.68 (s), 2.25 (m), 3.82 (s), 4.05 (d,J=5), 4.49 (s), 5.63 (d,J=4.5), 5.77 (d,J=4.5), 5.97 (d,J=5.5), 6.08 (d,J=5.5), 6.68 (m), and 7.37 (m) ppm.

TMS was used as internal reference.

EXAMPLE 29

L-1'-Methoxy-4'-aspartoyloxymethyl 2,6-dimethoxybenzylpenicillinate, hydrochloride To a solution of 4.3 g of chloromethyl 2,6-dimethoxyphenylpenicillinate in dimethylformamide (70 ml) were added 3.4 g of the potassium salt of N-[1-methyl-2-carbomethoxyvinyl]-L-aspartic acid 1'-methyl ester. After stirring for 16 hours, the mixture was diluted with 280 ml of ethyl acetate and washed with water (3 × 70 ml) and 0.5M aqueous sodium bicarbonate (40 ml), followed by water (3 × 40 ml). The organic phase was dried and evaporated in vacuo to give crude N-[1-methyl-2-carbomethoxy-vinyl]-L-1'-methoxy-4'-aspartoyloxymethyl 2,6-dimethoxybenzylpenicillinate. This material was hydrolyzed in the same way as described in Example 1B. Freeze-drying of the aqueous phase gave the desired product as a slightly yellowish, amorphous powder with a purity of 79%.

The nmr spectrum (D$_2$O) showed signals at $\delta =$ 1.45 (s), 1.60 (s), 3.22 (d,J=5.5), 3.77 (s), 3.82 (s), 4.50 (t,J= 5.5), 4.52 (s), 5.6–6.0 (m), about 5.9 (m), 6.72 (d,J=8), and 7.42 (t,J=8) ppm.

TMS was used as internal reference.

EXAMPLE 30

A. Chloromethyl 5-methyl-3-phenyl-4-isoxazolylpenicillinate

To a suspension of sodium 5-methyl-3-phenyl-4-isooxazolylpenicillinate (10.58 g) in DMF (50 ml) was added chloroiodomethane (10 ml). After stirring at room temperature for 4 hours, the mixture was diluted with ethyl acetate (200 ml) and washed with water (3 × 50 ml), 0.5M aqueous sodium bicarbonate (25 ml), and finally water (3 × 25 ml). The organic phase was dried and filtered, and the filtrate was evaporated in vacuo to yield a yellowish gum, which crystallized from ethyl acetate to yield pure chloromethyl 5-methyl-3-phenyl-4-isoxazolylpenicillinate as a colourless product, m.p. 129°–130°C. An analytical sample was prepared by recrystallization from ethyl acetate, m.p. 131°–132°C, $[\alpha]_D^{20} + 133°$ (C=0.5, CHCl$_3$).

B. L-Valyloxymethyl 5-methyl-3-phenyl-4-isoxazolylpenicillinate, hydrochloride 3.04 g of the potassium salt of N-[1-methyl-2-carbomethoxy-vinyl]-L-valine were added to a solution of 4.5 g of chloromethyl 5-methyl-3-phenyl-4-isoxazolylpenicillinate in dimethylformamide (80 ml). After stirring for 8 hours at room temperature, the mixture was diluted with ethyl acetate (320 ml) and washed with water (3 × 80 ml), 0.5M sodium bicarbonate (40 ml), and finally water (2 × 40 ml). The organic phase was dried and evaporated in vacuo. The residual yellowish gum was dissolved in tetrahydrofuran (60 ml) without further purification, water (60 ml) was added, and the apparent pH-value of the mixture was adjusted to 2.5 by addition of 2N hydrochloric acid with stirring. During the hydrolysis, this pH-value was maintained by addition of further hydrochloric acid via an automatic titrator. When the consumption of acid had ceased, tetrahydrofuran was removed from the mixture at reduced pressure (bath-temperature about 35°C), and the remaining aqueous phase was extracted with ethyl acetate (2 × 15 ml). To the combined ethyl acetate extracts were added ether (30 ml) and water (50 ml), the pH-value of the aqueous phase was adjusted to 2.5 by addition of diluted hydrochloric acid with stirring, and the aqueous phase was separated. The combined aqueous phases were washed with ether (20 ml) and filtered, and the filtrate was freeze-dried to give the desired compound as a colourless amorphous product with a purity of 86%.

EXAMPLE 31

A. Chloromethyl 5-methyl-3-o-chlorophenyl-4-isoxazolylpenicillinate

To a suspension of sodium 5-methyl-3-o-chlorophenyl-4-isoxazolylpenicillinate (14.65 g) in DMF (70 ml) was added chloroiodomethane (14 ml). After stirring at room temperature for 4 hours, the mixture was diluted with ethyl acetate (280 ml) and washed with water (3 × 70 ml), 0.5M aqueous sodium bicarbonate (35 ml), and finally water (3 × 35 ml). The organic phase was dried and filtered, and the filtrate was evaporated in vacuo to yield the crude chloromethyl 5-methyl-3-o-chlorophenyl-4-isoxazolylpenicillinate as a yellowish gum. This material could be used in the next step without further purification. A sample of the crude ester was purified by dry column chromatography on silica gel (eluent: cyclohexane-ethyl acetate, 7:3) and yielded pure chloromethyl 5-methyl-3-o-chlorophenyl-4-isoxazolylpenicillinate as a colourless amorphous powder, $[\alpha]_D^{20}$ + 112°(c=0.5, CHCl$_3$).

The nmr spectrum (CDCl$_3$) showed signals at $\delta$ = 1.43 (s), 1.50 (s), 2.80 (s), 4.35 (s), 5.50 (d,J=4.5), 5.91 (d,J=4.5), 5.68 (d,J=6.5), 5.87 (d,J=6.5), and 7.55 (m) ppm.

TMS was used as internal reference.

B. L-Isoleucyloxymethyl 5-methyl-o-chlorophenyl-4-isoxazolylpenicillinate, hydrochloride 3.2 g of the potassium salt of N-[1-methyl-2-carbomethoxy-vinyl]-L-isoleucine were added to a solution of 4.85 g of chloromethyl 5-methyl-3-o-chlorophenyl-4-isoxazolylpenicillinate in dimethylformamide (80 ml). After stirring for 8 hours at room temperature, the mixture was worked up in the same way as described in Example 30B. A similar acid hydrolysis of the resulting crude N-[1-methyl-2-carbomethoxy-vinyl]-L-isoleucyloxymethyl 5-methyl-3-o-chlorophenyl-4-isoxazolylpenicillinate and freeze-drying of the aqueous phase thus obtained gave the desired compound as an amorphous powder with a purity of 81%.

EXAMPLE 32

A chloromethyl α-azidobenzylpenicillinate

To a mixture of potassium α-azidobenzylpenicillinate (2.0 g) in DMF (20 ml) was added chloroiodomethane (2.0 ml), and the mixture was stirred for 105 minutes at room temperature. This mixture was worked up in the same way as described in Example 14A.

After purification by dry column chromatography on silica gel (eluent: cyclohexane-ethyl acetate, 7:3) the pure compound was obtained as a slightly yellowish, amorphous product.

TLC: $R_f$ = 0.53 (cyclohexane-ethyl acetate, 1:1), the nmr spectrum showed signals at $\delta$ = 1.58 (s), 1.67 (s), 4.51 (s), 5.13 (s), 5.50–5.80 (m), 5.88 (d)-5.70 (d) (ABq, J=6), 7.10 (broad), 7.45 (s) ppm.

TMS was used as internal standard.

B. Chloromethyl α-aminobenzylpenicillinate

This compound was prepared by the method of Example 24B from chloromethyl α-azidobenzylpenicillinate (2.0 g) in tetrahydrofuran (30 ml) and water (30 ml), using a 10% palladium-on-carbon catalyst (1.0 g).

Freeze-drying of the remaining aqueous phase gave the hydrochloride of the desired compound as a colourless amorphous product with a purity of 94% (iodometric).

To a solution of this product (0.4 g) in water (5 ml) was added 4-toluene-sulfinic acid (0.2 g) in water (5 ml). A colourless precipitate was formed, which was filtered off and dried. M.p. 112-114°C.

Analysis: Calculated for $C_{17}H_{20}ClN_3O_4S \cdot CH_3C_6H_4SO_2H \cdot H_2O$: C, 50.39; H, 5.29; Cl 6.20; N, 7.35; S, 11.20; H$_2$O, 3.15. Found: C, 50.31; H, 5.31; Cl, 6.74; N, 7.39; S, 11.17; H$_2$O, 3.25.

EXAMPLE 33

L-Isoleucyloxymethyl phenoxymethylpenicillinate

This compound was prepared analogously to the compound described in Example 1B from the potassium salt of compound 5 in Table 2 of Examples 17–23 and chloromethyl phenoxymethylpenicillinate.

The hydrochloride of the desired compound was obtained as an amorphous powder with a purity of 75%.

EXAMPLE 34

L-Methionyloxymethyl phenoxymethylpenicillinate

This compound was prepared analogously to the compound described in Example 1B from the potassium salt of the compound 11 in the Table 2 of Examples 17–23 and chloromethyl phenoxymethylpenicillinate. The hydrochloride of the desired compound was obtained as an amorphous powder with a purity of 68%.

EXAMPLE 35

L-Valyloxymethyl phenoxymethylpenicillinate, hydrochloride

This compound was prepared analogously to the compound described in Example 1B from N-[1-methyl-2-carbomethoxyvinyl]-L-valine potassium salt (compound 1 in Table 2 of the Examples 17–23) and chloromethyl phenoxymethylpenicillinate. The hydrochloride of the desired compound was obtained as an amorphous powder with a purity of 84%.

TLC: $R_f = 0.49$ (solvent system: n-butanol-acetic acid-$H_2O$ 4:1:5), $R_f = 0.61$ (solvent system: n-butanol-ethanol-$H_2O$ 8:2:2); nmr spectrum ($CD_3OD$-TMS standard): $\delta = 1.08$ (d,J=7), 1.52 (s), 1.60 (s), 2.30(m), 4.04 (d,J=4.5), 4.56 (s), 4.70 (s), 5.61 (s), 5.90 (d,J=5.5), 6.05 (d,J=5.5), 6.80–7.50 (m).

EXAMPLE 36

L-1'-Methoxy-4'-aspartoyloxymethyl phenoxymethylpenicillinate, hydrochloride

This compound was prepared analogously to the compound described in Example 1B, from the compound 7 in Table 2 of Examples 17–23 and chloromethyl phenoxymethylpenicillinate.

The hydrochloride of the desired compound was obtained as an amorphous powder with a purity of 88%.

TLC: $R_f = 0.52$ (solvent system: n-butanol-ethanol-$H_2O$ 8:2:2), $R_f = 0.48$ (solvent system: n-butanol-acetic acid-$H_2O$ 4:1:5); nmr spectrum ($CD_3OD$-TMS standard): $\delta = 1.51$ (s), 1.59 (s), 3.18 (d,J=5.5), 3.85 (s), 4.47 (t,J=5.5), 4.55 (s), 4.63 (s), 5.90 (s), 6.80–7.50 (m).

We claim:
1. A compound of the formula

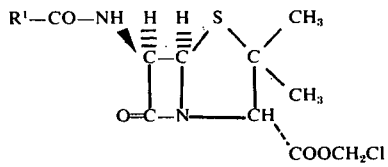

or a pharmaceutically acceptable salt thereof in which $R^1$ is selected from the group consisting of phenoxymethyl, benzyl, dimethoxyphenyl, 5-methyl-3-phenyl-4-isoxazolyl, and 5-methyl-3-O-chlorophenyl-4-isoxazolyl.

* * * * *